(12) United States Patent
Osorio et al.

(10) Patent No.: US 8,209,018 B2
(45) Date of Patent: Jun. 26, 2012

(54) PROBABILISTIC NEUROLOGICAL DISORDER TREATMENT

(75) Inventors: Ivan Osorio, Leawood, KS (US); Mark G. Frei, Lawrence, KS (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

(21) Appl. No.: 11/380,752

(22) Filed: Apr. 28, 2006

(65) Prior Publication Data
US 2007/0213785 A1    Sep. 13, 2007

Related U.S. Application Data

(60) Provisional application No. 60/780,954, filed on Mar. 10, 2006.

(51) Int. Cl.
*A61N 1/18* (2006.01)
*A61B 5/02* (2006.01)

(52) U.S. Cl. .......................... 607/45; 600/544

(58) Field of Classification Search .................. 600/544, 600/545; 607/45
See application file for complete search history.

(56) References Cited

U.S. PATENT DOCUMENTS

| | | |
|---|---|---|
| 3,863,625 A | 2/1975 | Viglione et al. |
| 5,995,868 A | 11/1999 | Dorfmeister et al. |
| 6,343,229 B1 | 1/2002 | Siebler |
| 6,374,140 B1 | 4/2002 | Rise |
| 6,560,486 B1 | 5/2003 | Osorio et al. |
| 6,594,525 B1 | 7/2003 | Zierhofer |
| 6,678,548 B1 | 1/2004 | Echauz et al. |
| 6,795,737 B2 | 9/2004 | Gielen |
| 7,437,196 B2 | 10/2008 | Wyler |
| 7,582,062 B2 | 9/2009 | Magill |
| 2002/0103512 A1 | 8/2002 | Echauz et al. |
| 2003/0139781 A1 | 7/2003 | Bradley |
| 2003/0158587 A1 | 8/2003 | Esteller et al. |
| 2003/0204219 A1 | 10/2003 | Gielen |
| 2004/0082984 A1 | 4/2004 | Osorio et al. |
| 2004/0267152 A1 | 12/2004 | Pineda |
| 2005/0004617 A1 | 1/2005 | Dawant |
| 2005/0049649 A1 | 3/2005 | Luders |
| 2005/0049650 A1 | 3/2005 | Nuttin |
| 2005/0065427 A1 | 3/2005 | Magill |
| 2005/0165458 A1 | 7/2005 | Boveja |
| 2005/0240242 A1 | 10/2005 | DiLorenzo |
| 2005/0283201 A1 | 12/2005 | Machado |
| 2006/0015153 A1 | 1/2006 | Gliner |
| 2006/0058855 A1 | 3/2006 | Gill |
| 2006/0212090 A1 | 9/2006 | Lozano |
| 2007/0129770 A1 | 6/2007 | Younis |

FOREIGN PATENT DOCUMENTS

| | | |
|---|---|---|
| EP | 1609414 A | 12/2005 |
| WO | 0010455 | 3/2000 |
| WO | 0121067 A | 3/2001 |
| WO | 0249500 A2 | 6/2002 |
| WO | 02058536 A2 | 8/2002 |
| WO | 03030734 A2 | 4/2003 |
| WO | 03063684 A | 8/2003 |

OTHER PUBLICATIONS

International Search Report and Written Opinion, Aug. 31, 2007.

*Primary Examiner* — Carl H Layno
*Assistant Examiner* — Allen Porter, Jr.

(57) ABSTRACT

Disclosed are probabilistic approaches to patient evaluation, warning and treatment of a neurological disorder. Disclosed techniques estimate probability distribution functions or cumulative distribution functions, determined by relying on representative historical profiles, comprising information in short and/or long timescales obtained at times that may be intermittent or temporally discontinuous from each other or from other events of interest. The patient may thereby be treated based on the determined probability information.

20 Claims, 12 Drawing Sheets

PROBABILISTIC NEUROLOGICAL DISORDER TREATMENT

This non-provisional patent application claims priority to U.S. Provisional Application Ser. No. 60/780,954 filed Mar. 10, 2006, which is incorporated herein by reference in its entirety.

BACKGROUND OF THE INVENTION

The invention relates to the evaluation, warning and treatment of neurological disorders such as epilepsy, devices for such evaluation, warning and treatment, including external and implantable devices and systems, and methods and techniques by which the devices and systems operate, and the methods by which patients suffering disorders such as epilepsy are evaluated, warned, and treated by electrical stimulation or some other modality. Specifically, the invention discloses a probabilistic approach for issuing warnings and/or triggering therapy delivery without relying on conventional event detection or prediction approaches. This may result in therapy delivery before the onset of a neurological event, such as seizure, or even before the onset of a pre-event state, thus preventing the neurological event from occurring.

BRIEF DESCRIPTION OF THE PRIOR ART

The objective of currently approved seizure therapies, whether pharmacological or electrical, is to treat seizures through an "open-loop" approach. In the case of drugs, these are dosed based on their half-life and therapeutic ratio, so as to maintain relatively constant drug serum concentrations round-the-clock and avoid large fluctuations (drops or rises in concentrations), that may leave the subject relatively unprotected (if low) or may cause dose-related side effects (if high). In the case of electrical stimulation such as with the Neurocybernetic prosthesis (Cyberonics, Houston, Tex.), currents are delivered periodically, round-the-clock.

For drugs and electrical stimulation, the dosing/stimulation schedule (not the dose or electrical current intensity) of approved therapies does not take into account the actual frequency of seizures or their temporal (e.g., circadian) distributions: The approach is fundamentally the same for a subject with multiple daily seizures or for one with only one every few years, or if the seizures occur only at night or at any time during the daylight. Adjustments in treatment, if any, are made at certain time intervals based on the number of seizures reported by the subject (by seizure diary) or on the frequency and type of side effects over that interval.

Since the advent of automated means for detecting seizures (see, e.g., U.S. Pat. No. 5,995,868 Osorio et al.; Neuropace; Litt) and of methods that allegedly predict the onset of seizures (see, e.g., patents issued to Iasemidis; Litt; Hively, Lenhertz), warning and closed-loop therapeutic intervention in response to the output of those methods is now possible. This approach is potentially highly temporo-spatially selective, minimizing adverse effects and unnecessary treatments and in theory, may be superior to open-loop. However, all known, useful prior-art closed-loop therapies restrict intervention to be contingent upon discrete event detections and require that signals (EEG or other types) be continuously monitored (around the clock and for the life of the subject) to enable these event detections.

In the case of seizure detection-based closed-loop control, known devices attempt to detect the occurrence of a seizure through analysis of biological signals and respond with electrical stimulation or other therapy. In the case of seizure prediction-based closed-loop control, known devices attempts to detect the occurrence of a pre-seizure state, again through some analysis of biological signals, and respond with delivery of some contingent therapy.

These approaches to closed-loop control remain based on relatively short time scales of changes (seconds to minutes in the case of seizure detection, seconds to a few hours in the case of seizure prediction) and typically are based on the assumption that the detection is connected in a dynamically contiguous way with the ongoing or impending seizure. In addition, these approaches ignore temporal correlations between seizures including long-range dependencies.

SUMMARY OF THE INVENTION

The following represents a simplified summary of some embodiments of the invention in order to provide a basic understanding of various aspects of the invention. This summary is not an extensive overview of the invention. It is not intended to identify key or critical elements of the invention or to delineate the scope of the invention. Its sole purpose is to present some embodiments of the invention in simplified form as a prelude to the more detailed description that is presented below.

In accordance with aspects of the invention, disclosed are approaches to patient evaluation, warning and treatment, referred herein to as probabilistic approaches, that are not based on a strict binary approach for discrete event detection (i.e., "0" for no detection and "1" for detection), or prediction (i.e., "0" for no issuance of prediction and "1" for issuance of a prediction). Instead, disclosed are techniques that estimate probability distribution functions or cumulative distribution functions, "built" relying on representative historical profiles, comprising information in short and/or long timescales obtained at times that may be intermittent or temporally discontinuous from each other or from other event of interest. This information is used to obtain statistical profiles that then are factored into warning and control/treatment programs. The warnings or interventions that result from this approach will not be purely open-loop (in which no real-time or instantaneous information about the system is used) or purely conventional closed-loop (in which therapy is solely contingent upon event detection. Nor will they be prediction-based by analysis of the most recent epoch of signals alone and using the binary approach (zero for no event and 1 for detection or prediction of event).

In accordance with aspects of the various embodiments, the issuing of warning or delivery of a therapy is based not only on degree of brain excitability estimated using relevant signals (e.g., electrical, temperature, neurotransmitters concentrations) but it takes into account, as needed, other factors including, but not limited to, time of day (circadian rhythms), metabolic state, time elapsed since previous seizures, the intensity, duration and spread (severity) of previous seizures, site of seizure origin, type, "dose" and time elapsed since the last treatment, long and/or short dependencies/correlation of events of interest, type and level of cognitive/behavioral brain activities and presence of/exposure to known precipitants (e.g., light). This yields an adaptable, "normalized" probability and provides prospective learning about the temporo-spatial evolution of the system and provides an ability to adapt and improve performance to preferably prevent not only seizures but also any pre-ictal or pre-seizure state. This approach decreases the reliance on event (seizures in this application) detection or prediction (in the binary sense of 0 or 1), leading to a flexible and sensitive system for estimation of the probability of state change.

The approach may be enhanced through the utilization of Fuzzy logic, which is suited for control of systems with large numbers of degrees of freedom. One of the embodiments disclosed herein obviates the need for continuous signal acquisition, processing and analysis beyond a certain point in time (e.g., after adequate "training" "learning" or a "representative" distribution has been obtained), thus decreasing on-line computational complexity and power consumption. Intervention as proposed herein does not exclude and instead includes the possibility of parallel seizure detection (in the binary sense of "0" or "1") to minimize failure and maximize therapeutic efficacy and subject safety.

The probabilistic approaches disclosed herein may be used in conjunction with conventional "open-loop" therapy or conventional closed-loop therapies allowing their optimization by both uncovering and taking into account one or more of the following criteria: a) the times (e.g., of day or month) at which therapy is most needed/beneficial and avoiding those during which it is not necessary or may even have a paradoxical effect (e.g., increasing seizure likelihood, frequency or severity) or cause other adverse effects; b) optimal duration of stimulation (decrease unnecessary or ineffective duration of stimulation) or other stimulation parameters; and c) timing of stimulation in relation to seizure onset or termination. The approach may be initiated with the tracking/logging of seizure frequency and severity for appropriate periods of time; once this is accomplished and sufficient, stable seizure control may be achieved, tracking/logging may be stopped to save battery power, etc.

BRIEF DESCRIPTION OF THE DRAWINGS

The present invention is illustrated by way of example and not limited in the accompanying figures in which like reference numerals indicate similar elements and in which.

DETAILED DESCRIPTION OF THE PREFERRED EMBODIMENTS

Overview

Figure 1:
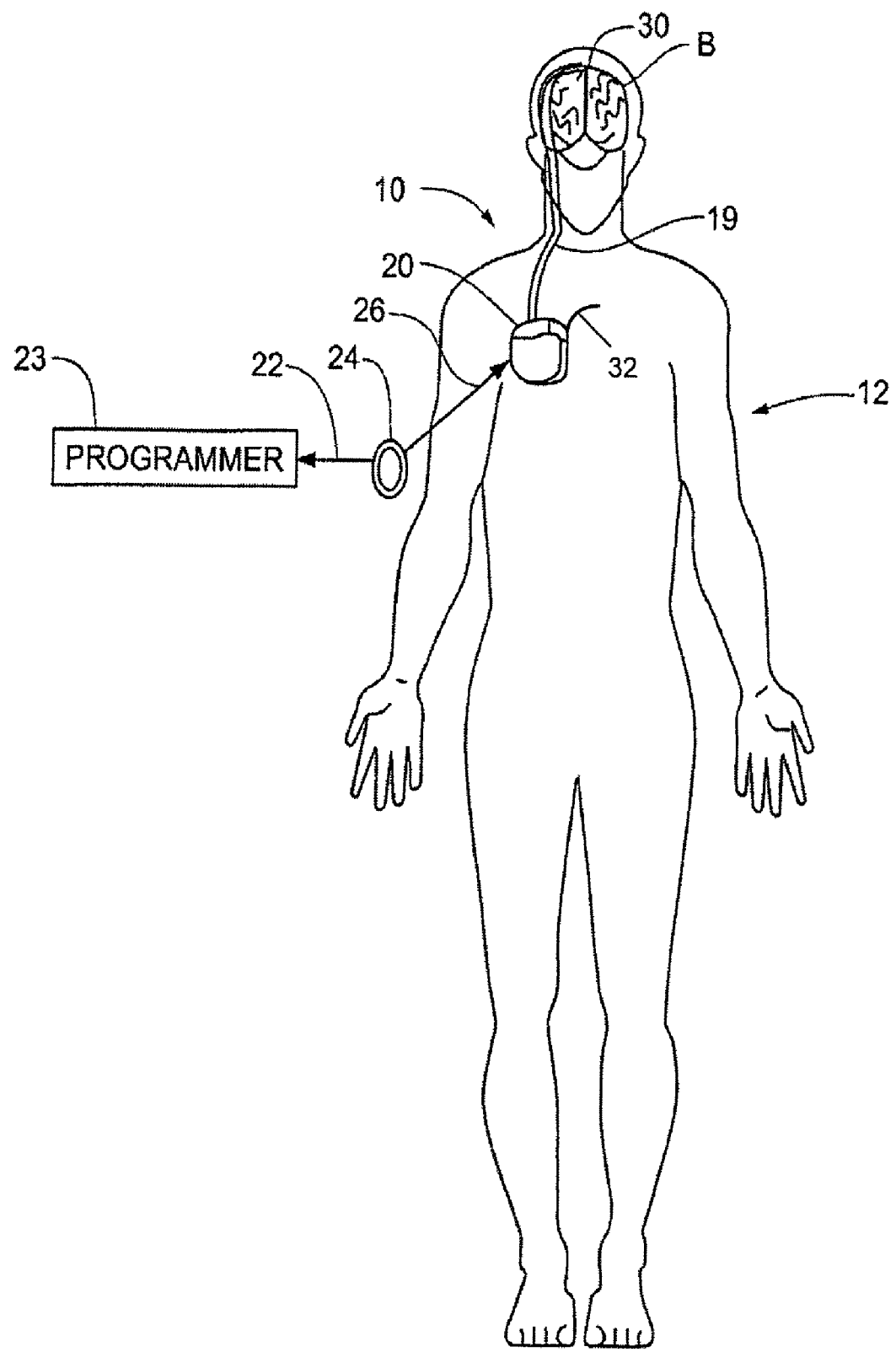
FIG. 1 is a schematic view of a medical device implanted in a patient that monitors cardiac and nervous system disorders in accordance with an aspect of the invention.

The following discloses approaches to patient evaluation, warning and treatment, referred herein to as "probabilistic" approaches, that are not based on a strict binary approach for discrete event detection (i.e., "0" for no detection and "1" for detection), or prediction (i.e., "0" for no issuance of prediction and "1" for issuance of a prediction). Instead, disclosed are techniques that estimate probability distribution functions or cumulative distribution functions, "built" relying on representative historical profiles, comprising information in short and/or long timescales obtained at times that may be intermittent or temporally discontinuous from each other or from other events of interest.

Conventional "open-loop" control (i.e., that which is implemented in the absence of immediate information or "feedback") is comparatively easy to implement, as it does not require that a device monitor in real-time, the state of the subject and decipher the relevant information. Conventional closed-loop control is a more powerful class of therapy than conventional open-loop, and while more expensive/complicated than open-loop, it offers greater opportunity for success in certain cases. Both approaches, closed-loop and open-loop, as currently utilized, have advantages and disadvantages relative to one another. In the embodiments disclose herein are techniques, termed "probabilistic closed-loop," that provide a new approach to therapy or control that draws on the strengths of the two approaches and attempts to advance beyond what may be perceived as their respective limitations.

In the embodiment of treating or controlling seizures, probabilistic control of seizures is based on the following observations: (1) the probability of seizure occurrence is not solely a function of signal changes in the system but of multiple factors; (2) seizure probability changes as a function of state, being lowest in the period immediately following the termination of seizures; and (3) the anti-seizure effects of closed-loop electrical stimulation, either local (delivered directly to epileptogenic tissue) or remote (delivered to epileptogenic tissue via a structure connected to it), of epileptogenic tissue are both closely temporally correlated with delivery of currents (immediate effect) and persist for some time beyond cessation of stimulation ("carry-over" effect) [Osorio et al 05, Annals of Neurology].

Depending on the duration and degree of protective "carry-over" effect, stimulation parameters may be adjusted to attain a state of protection that minimizes seizure occurrence probability and whose level or degree of protection is a function of this probability. This strategy, referred to as probabilistic closed-loop, may be in certain cases, preferable to conventional closed-loop treatment, which operates only in response to event detections (either seizure detections or, in the case of "prediction," the detection of a pre-seizure state) and provides event detection-contingent therapy. Of course, both options may be used together, i.e., one does not necessarily preclude the other. For example, contingent therapy such as stimulation may be used to treat breakthrough seizures. Moreover, if future studies show, as did one study [Osorio 05], that short closed-loop trials help identify efficacious parameters, they may be followed by open-loop phases, making open-loop intelligent or adaptive ("intelligent open-loop").

The "probabilistic closed-loop" may evolve, under certain circumstances and in certain cases, into "intelligent" open-loop defined as lacking immediate or real-time information/ "feedback", but operating according to changes in estimates of seizure probability (as a function of time and/or state) which were calculated using past information and which may be updated/improved (as a function of time and/or state) but not in real-time, using new information. "Intelligent" open-loop does not require that implantable monitoring devices be used for real-time signal processing/analysis for the detection/prediction/quantification of seizures nor that in-hospital monitoring be performed. Instead, portable monitoring devices for ambulatory/home monitoring may be used. The monitoring devices may obtain signals such as EEG, ECoG, EKG or others, preferably via telemetry and periods of intensive monitoring and parameter optimization (with or without closed-loop therapy) may be carried out as often as indicated. By decreasing reliance on continuous signal monitoring, this alternative therapeutic regimen simplifies operation and decreases power requirements, factors that translate into smaller, more efficient and less costly implantable therapy devices.

As used herein, "open-loop" control is generally therapy that is administered according to a program that depends on time, without taking into account real-time information about the state of the subject. "Closed-loop" is generally refers to the administration of therapy that is dependent upon information about the state of the subject and therapy is triggered if and when seizures are either detected or predicted.

As used herein, "intelligent open-loop" is generally the triggering of interventions dictated by changes in probability of seizure occurrence estimated using past information. For example, if the mean or median half-life duration of the protective carry-over effect of electrical stimulation in a given patient lasts 20 minutes, as determined with closed-loop or probabilistic closed-loop modalities, electrical stimulation will be delivered again 20 min after each trial, round-the clock. This modality does not use real-time but past information.

As described herein, "probabilistic closed-loop" does not require detection or prediction of seizures for triggering an intervention/therapy delivery, but rather, probabilities that are associated with: (a) an unacceptable value (for the subject or for the situation, etc.) related to safety, social or other risks; (b) a change in value which is rapid and/or large in magnitude for that subject, brain/systems state, time of day or activity; (c) weakening of the "steady-state" of protection (loss of a "carry-over" effect) afforded by previous therapy delivery or inability to attain the sufficient degree of "carry-over" protection following therapy delivery.

Embodiments of the Medical Device System

In an embodiment, the invention may be implemented within an implantable neurostimulator system, however, those skilled in the art will appreciate that the techniques disclosed herein may be implemented generally within any implantable medical device system including, but not limited to, implantable drug delivery systems, and implantable systems providing stimulation and drug delivery. The implantable medical device may provide therapeutic treatment to neural tissue in any number of locations in the body including, for example, the brain (which includes the brain stem), the vagus nerve, the spinal cord, peripheral nerves, etc. The treatment therapies can include any number of possible modalities alone or in combination including, for example, electrical stimulation, magnetic stimulation, drug infusion, brain temperature control, and/or any combination thereof.

In addition, aspects of the invention may be embodied in various forms to analyze and treat nervous system and other disorders, namely disorders of the central nervous system, peripheral nervous system, and mental health and psychiatric disorders. Such disorders include, for example without limitation, epilepsy, Sudden Unexpected Death in Epilepsy Patients (SUDEP), Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimer's, and anorexia.

In certain embodiment, the biological signals that may selected, stored and/or reported in accordance with various aspects of the invention may include any number of sensed signals. Such biological signals can include, for example, electrical signals (such as EEG, ECoG and/or EKG), chemical signals (such as change in quantity of neurotransmitters), temperature signals, pressure signals (such as blood pressure, intracranial pressure or cardiac pressure), respiration signals, heart rate signals, pH-level signals, activity signals (e.g., detected by an accelerometer), and/or peripheral nerve signals (cuff electrodes on a peripheral nerve). Such biological signals may be recorded using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal. In addition, various types of physiologic activities may be sensed including, for example, brain, heart and/or respiration.

As discussed, the techniques disclosed herein are suitable for use within any implantable medical device system that receives signals associated with the physiological conditions being sensed, a memory component, and a processing component (logic or software) that stores data records in data structures.

Manual indication of a seizure or other event may be achieved through an external programmer device. The patient (or caregiver) may push a button on the external programmer device, while communicating with the implanted device. This may provide a marker of the sensed data (for example, in the event the patient is experiencing a neurological event).

In assessing the risk of SUDEP, for example, prolonged ECG recordings may be possible (e.g., recording all data during sleep since the incidence of SUDEP is highest in patients during sleep). Post-processing of the signal can occur in the implanted device, the patient's external device, a clinician external device, and/or another computing device. Intermittently (e.g., every morning, once/week, following a seizure), a patient may download data from the implantable device to the patient external device (as will be discussed further herein), which may then be analyzed by the external device (and/or sent through a network to the physician) to assess any ECG abnormalities. If an abnormality is detected, the device may notify the patient/caregiver. At that time, the patient/caregiver may inform the healthcare provider of the alert to allow a full assessment of the abnormality. The clinician external device may also be capable of obtaining the data from the implanted device and conducting an analysis of the stored signals. If a potentially life-threatening abnormality is detected, the appropriate medical treatment may be prescribed (e.g., cardiac abnormality: a pacemaker, an implantable defibrillator, or a heart resynchronization device may be indicated or respiration abnormality: CPAP, patient positioning, or stimulation of respiration may be indicated). These data may be used to build probability estimates as a function of time, state (asleep or in seizure) and activities (exercising) to enable therapies at times of high risk to prevent an event or, in the case of SUDEP, a fatal outcome.

Moreover, the implantable medical device may also monitor EEG signals from intracranially implanted leads. This may allow the implanted medical device to collect cardiovascular and neurological signals in close proximity to detected neurological events as well as notify the patient/caregiver of a prolonged event (and/or status epilepticus). The implantable medical device may detect neurological events and analyze the peri-ictal signals and initiate loop recording.

Again, it will be appreciated that alternative embodiments of the implantable medical device may also be utilized. For example, cardiac lead(s), a sensor stub, and/or a wearable patch may be used to facilitate detection of a neurological event and the recording of data and signals pre and post event. An integrated electrode may also be used that senses ECG signals as described in U.S. Pat. No. 5,987,352. Optionally, the implantable medical device may warn/alert the patient 12 via buzzes, tones, beeps or spoken voice (as substantially described in U.S. Pat. No. 6,067,473) via a piezo-electric transducer incorporated into the housing of implantable medical device. The sound may be transmitted to the patient's inner ear.

In another embodiment, the monitor may be implanted cranially in the patient 12 (FIG. 1). In such an embodiment, the monitor may be constructed as substantially described in U.S. Pat. Nos. 5,782,891 and 6,427,086. EEG sensing may be accomplished by the use of integrated electrodes in the housing of the monitor, cranially implanted leads, and or leadless EEG sensing.

FIG. 1 illustrates an implantable system 10 including an implantable medical device 20 implanted in a patient 12. Optionally, the implantable medical device 100 may monitor one or more biological signals/conditions of the patient via lead 19 and monitoring/sensing elements 30 and 32 (in the embodiment, the biological conditions are cardiac and neurological functions of patient 12). Stored diagnostic data may be uplinked and evaluated by an external computing device 23 (e.g., a patient's or physician's programmer) via a 2-way telemetry, using for example, antenna 24 to relay radio frequency signals 22, 26 between implantable medical device 100 and external computing device 23. An external patient activator that may be located on external computing device 23 may optionally allow patient 12, or care provider (not shown), to manually activate the recording of diagnostic data.

Figure 2:
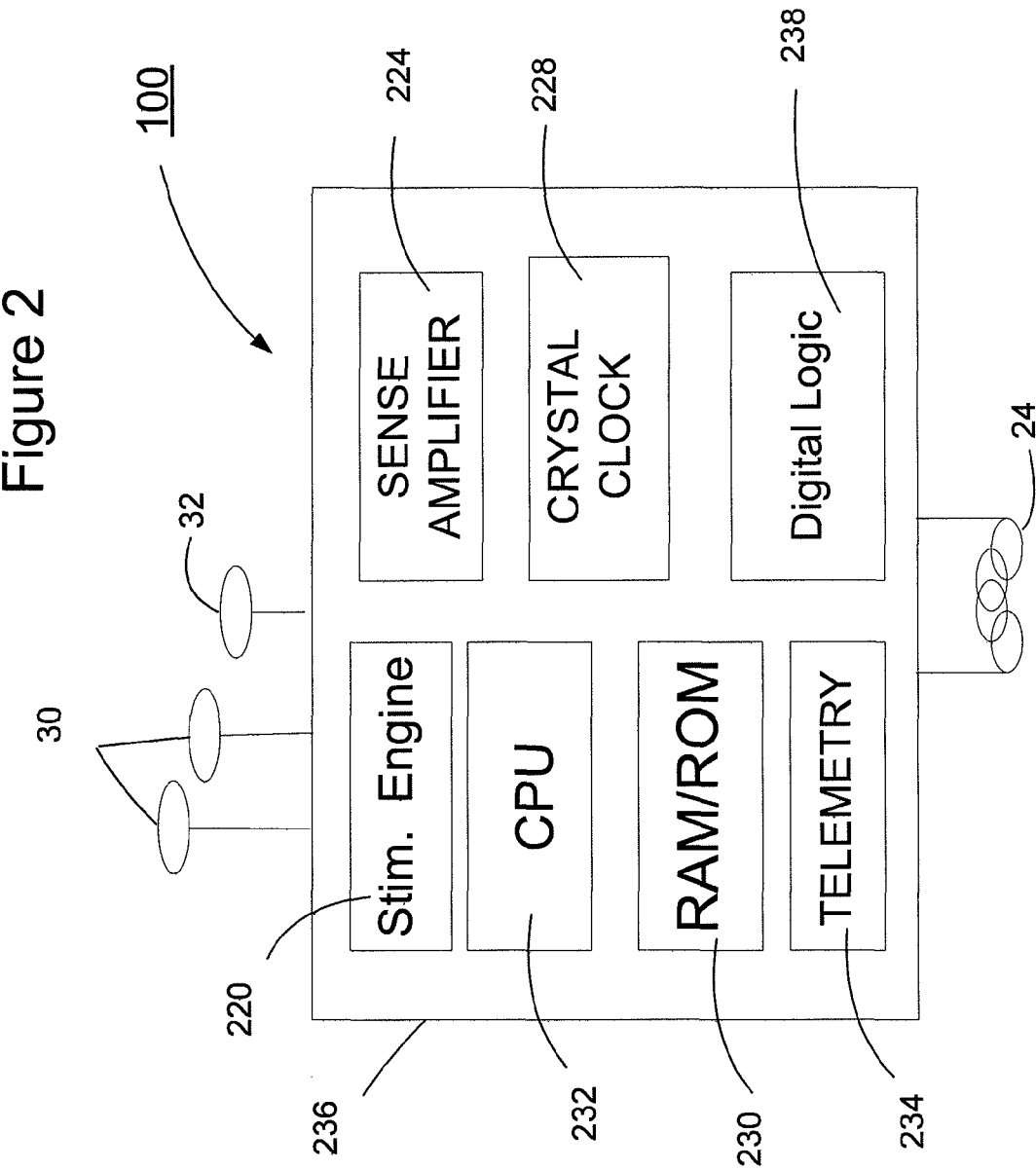
FIG. 2 is a simplified block diagram of the medical device shown in FIG. 1 in accordance with an aspect of the invention.

FIG. 2 depicts a block diagram of the electronic circuitry of implantable medical device 100 of FIG. 1 in accordance with an embodiment of the invention. Implantable medical device 100 comprises a primary control circuit 220 and may be similar in design to that disclosed in U.S. Pat. No. 5,052,388. Primary control circuit 220 includes sense amplifier circuitry 224, a crystal clock 228, a random-access memory and read-only memory (RAM/ROM) unit 230, a central processing unit (CPU) 232, digital logic circuit 238, a telemetry circuit 234, and stimulation engine circuitry 236, all of which are generally known in the art.

Implantable medical device 100 may include internal telemetry circuit 234 so that it is capable of being programmed by means of external programmer/control unit 23 via a 2-way telemetry link. External programmer/control unit 23 communicates via telemetry with implantable medical device 100 so that the programmer can transmit control commands and operational parameter values to be received by the implanted device, and so that the implanted device can communicate diagnostic and operational data to the programmer 23. For example, programmer 23 may be Models 9790 and CareLink® programmers, commercially available from Medtronic, Inc., Minneapolis, Minn. Various telemetry systems for providing the necessary communications channels between an external programming unit and an implanted device have been developed and are well known in the art. Suitable telemetry systems are disclosed, for example, in U.S. Pat. Nos. 5,127,404; 4,374,382; and 4,556,063.

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna 24 for receiving downlink telemetry signals and for radiating RF signals for uplink telemetry. The system is modeled as an air-core coupled transformer. An example of such a telemetry system is shown in U.S. Pat. No. 4,556,063.

In order to communicate digital data using RF telemetry, a digital encoding scheme such as is described in U.S. Pat. No. 5,127,404 can be used. In particular, a pulse interval modulation scheme may be employed for downlink telemetry, wherein the external programmer transmits a series of short RF "bursts" or pulses in which the interval between successive pulses (e.g., the interval from the trailing edge of one pulse to the trailing edge of the next) is modulated according to the data to be transmitted. For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

Programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 220 includes central processing unit 232 which may be an off-the-shelf programmable microprocessor or microcontroller, but in an embodiment of the invention it may be a custom integrated circuit. Although specific connections between CPU 232 and other components of primary control circuit 220 are not shown in FIG. 2, it will be apparent to those of ordinary skill in the art that CPU 232 functions to control the timed operation of sense amplifier circuit 224 under control of programming stored in RAM/ROM unit 230. In addition to or as an alternative embodiment digital logic 238 may also be provided and utilized. In another alternative embodiment, a processing module that contains either a processor or digital circuitry may also be utilized. Those of ordinary skill in the art will be familiar with such an operative arrangement.

With continued reference to FIG. 2, crystal oscillator circuit 228 provides main timing clock signals to primary control circuit 220. The various components of implantable medical device 100 are powered by means of a battery (not shown), which is contained within the hermetic enclosure of implantable medical device 100. For the sake of clarity in the figures, the battery and the connections between it and the other components of implantable medical device 100 are not shown. Sense amplifier 224 is coupled to monitoring/sensing elements 30 and 32. Where cardiac intrinsic signals are sensed, they may be sensed by sense amplifier 224 as substantially described in U.S. Pat. No. 6,505,067.

Processing by CPU 232 or digital logic 238 allows detection of cardiac and neural electrical characteristics and anomalies. CPU 232 or digital logic 238, under control of firmware resident in RAM/ROM 230, may initiate recording of the appropriate diagnostic information into RAM of RAM/ROM 230.

Figure 3:
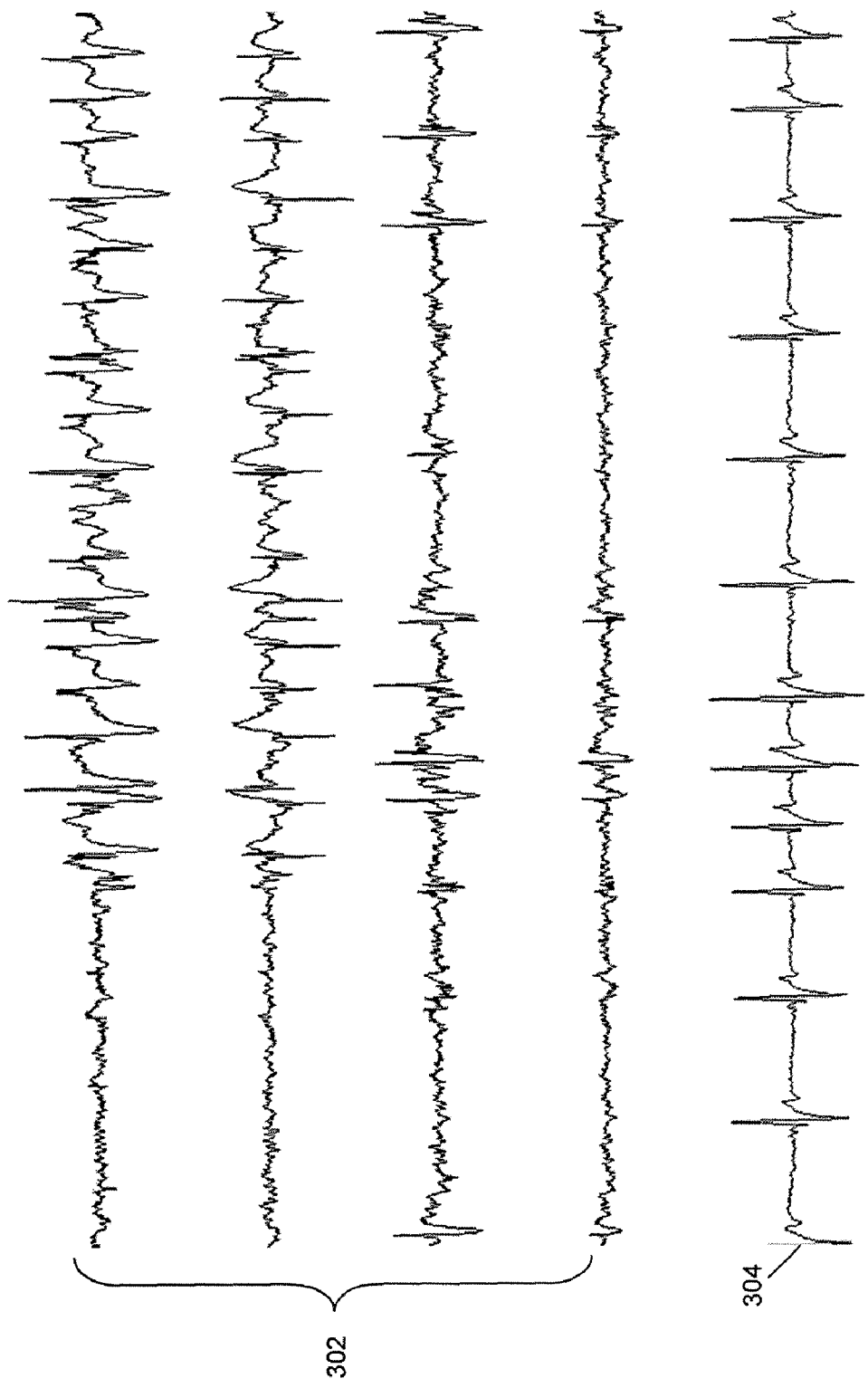
FIG. 3 is a graphical representation of various signals sensed by the medical device as shown in FIG. 1 in accordance with an aspect of the invention.

It will be appreciated that alternative embodiments of implantable medical device 100 may also be utilized. As discussed above, implantable medical device 100 may sense any number of physiologic conditions of the patient 12 for purposes of detecting, and storing data relating to, any number of the neurological events. For example, various lead(s) may be used to facilitate detection of a neurological event and the recording of data and signals pre and post event. For instance, FIG. 3 shows a graphical representation of various signals 302 and 304 that may be sensed by the medical device as shown in FIG. 1 in accordance with an aspect of the invention.

In another aspect of the invention, an electrode 32 located distally on a sensor stub may be used to facilitate detection of a neurological event and the recording of data and signals pre and post event. See U.S. Pat. No. 5,987,352. In alternative embodiments of the invention, the implantable medical device 100 may also sense respiration parameters such as respiration rate, minute ventilation and apnea via measuring and analyzing the impedance variations measured from the implanted implantable medical device 100 case to the electrode located distally on the sensor stub lead as substantially described in U.S. Pat. Nos. 4,567,892 and 4,596,251.

In yet another aspect of the invention, an external wearable device such as a wearable patch, a wristwatch, or a wearable computing device may be used to continuously sense implantable medical device cardiac functions of patient 12. Optionally, a button (not shown) on the external wearable device may be activated by the patient 12 (or a caregiver) to manually activate data recording (for example, in the event the patient is experiencing a neurological event). The external wearable device may comprise an amplifier, memory, microprocessor, receiver, transmitter and other electronic components as substantially described in U.S. Pat. No. 6,200,265. In the embodiment of a wearable patch, the device may consist of a resilient substrate affixed to the patient's skin with the use of an adhesive. The substrate flexes in a complimentary manner in response to a patient's body movements providing patient comfort and wearability. The low profile patch is preferably similar in size and shape to a standard bandage, and may be attached to the patient's skin in an inconspicuous location.

The above embodiments illustrate that the disclosed techniques may be implemented within any number of medical device systems (drug delivery, electrical stimulation, pacemaking, defibrillating, cochlear implant, and/or diagnostic). In general, the implanted medical component utilizes one or more monitoring elements (e.g., electrodes or other sensors), a memory component having a plurality of data structures (and/or data structure types), a processing component (such as a CPU or digital logic), and a telemetry component.

Figure 4:
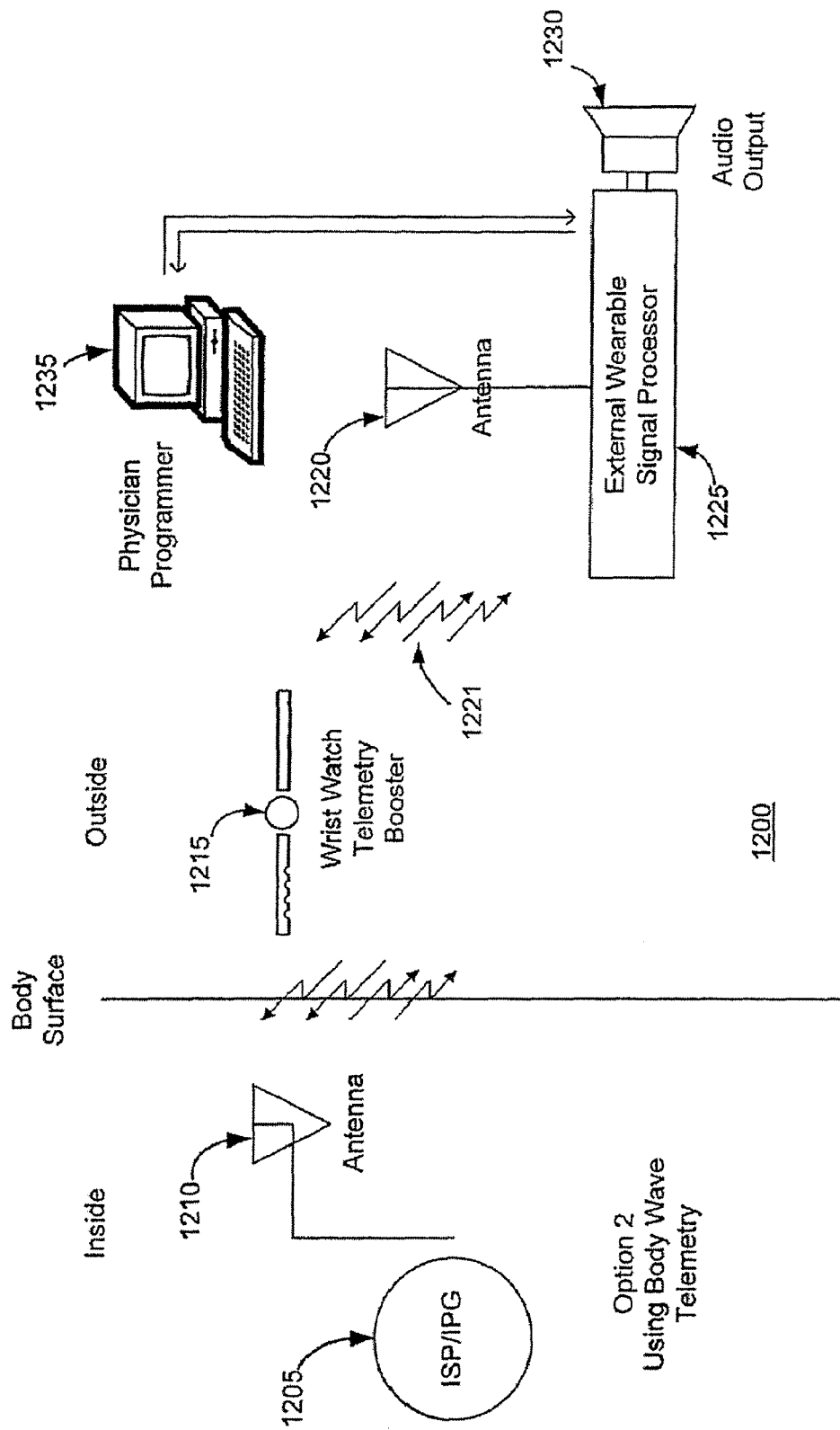
FIG. 4 shows an apparatus that supports reporting neurological data in accordance with an aspect of the invention.

FIG. 4 shows apparatus 1200 that supports reporting physiological data in accordance with an aspect of the invention. With apparatus 1200, the implanted component 1205 of the medical device system communicates with the relaying module 1215 via telemetry antenna 1210. Similarly, the external component 1225 communicates with the relaying module 1215 via antenna 1220. In the embodiment, a telemetry link 1221 between relaying module 1215 and antenna 1220 comprises a 3 MHz body wave telemetry link. To avoid interference, the relaying module 1215 may communicate with the external and implanted components using differing communication schemes. In some embodiments, the reverse direction and the forward direction of telemetry link 1221 may be associated with different frequency spectra. The relaying module 1215 thereby provides a greater range of communications between components of medical device system. For example, in the embodiment of an implanted system, an external programmer may communicate with an implanted device from a more remote location. The external programmer may be across the room and still be in communication via the relaying module 1215. With the telemetry booster stage, the use of an implanted system is more convenient to the patient, in particular at night while sleeping or when taking a shower, eliminating the need for an external device to be worn on the body.

Figure 5:
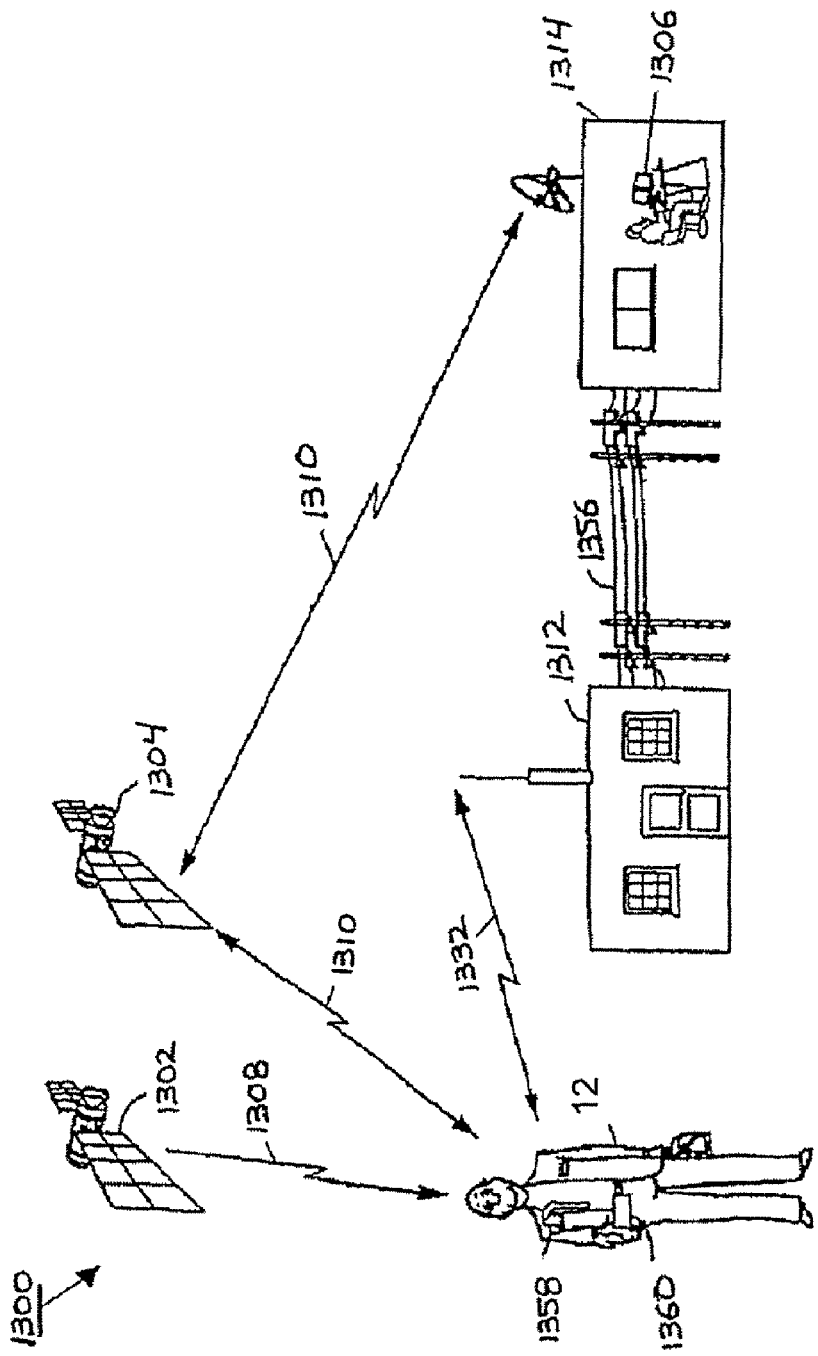
FIG. 5 is a schematic diagram of a system utilizing the above-described embodiments and allowing remote monitoring and diagnostic evaluation of at risk patients in accordance with an aspect of the invention.

As shown in FIG. 5, in an embodiment, the system allows the residential, hospital or ambulatory monitoring of at-risk patients and their implanted medical devices at any time and anywhere in the world. Medical support staff 1306 at a remote medical support center 1314 may interrogate and read telemetry from the implanted medical device and reprogram its operation while the patient 12 is at very remote or even unknown locations anywhere in the world. Two-way voice communications 1310 via satellite 1304, via cellular link 1332 or land lines 1356 with the patient 12 and data/programming communications with the implanted medical device 1358 via a belt worn transponder 1360 may be initiated by the patient 12 or the medical support staff 1306. The location of the patient 12 and the implanted medical device 1358 may be determined via GPS 1302 and link 1308 and communicated to the medical support network in an emergency. Emergency response teams can be dispatched to the determined patient location with the necessary information to prepare for treatment and provide support after arrival on the scene. See, e.g., U.S. Pat. No. 5,752,976.

Figure 6:
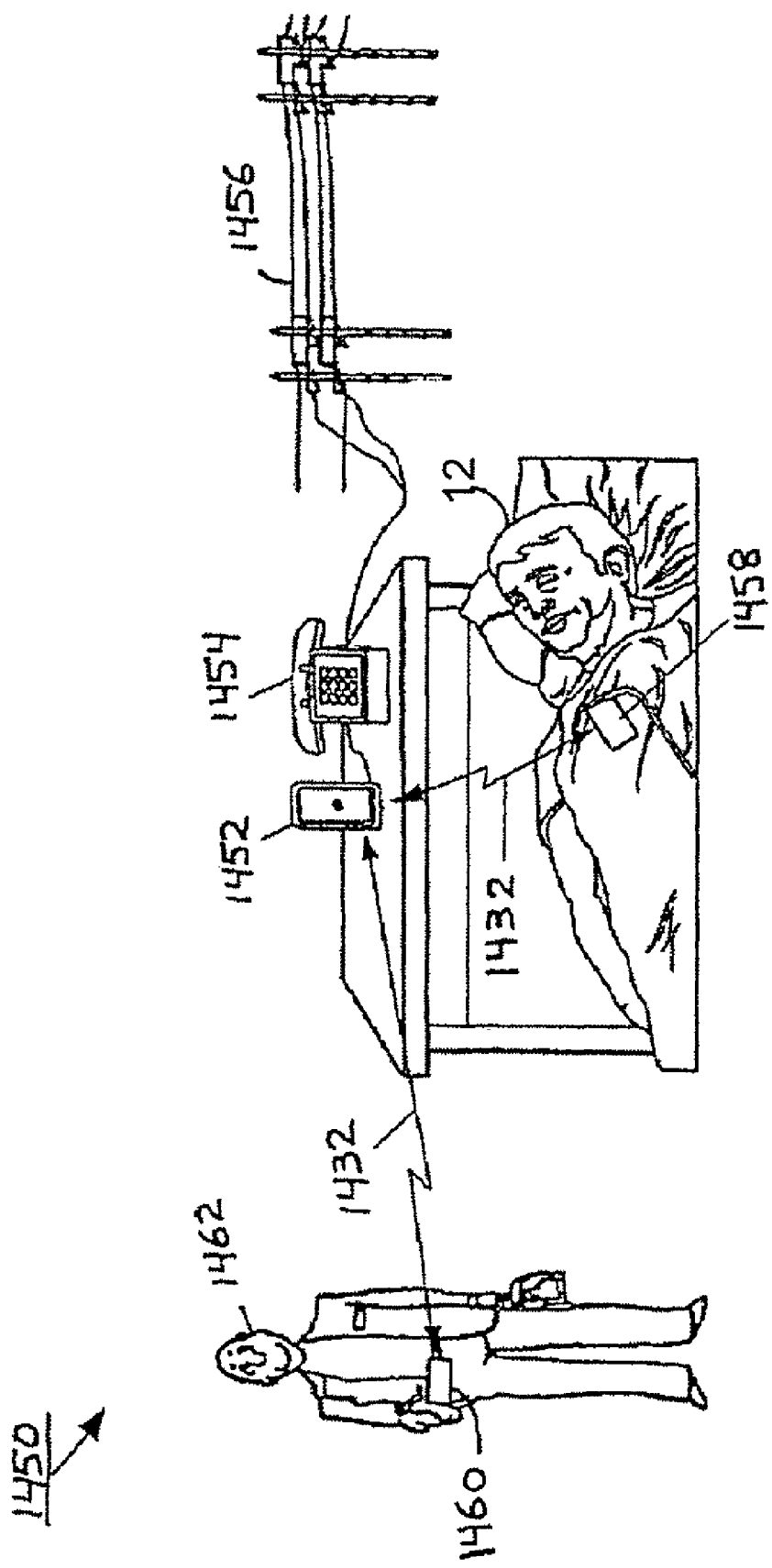
FIG. 6 is a schematic diagram of an alternative system utilizing the above-described embodiments and allowing remote monitoring and diagnostic evaluation of at risk patients in accordance with an aspect of the invention.

An alternative or addition to the system as described above in conjunction with FIG. 5 is shown in the system 1450 of FIG. 6, which shows a patient 12 sleeping with an implantable Monitor 1458 and/or optional therapy device as described above in connection with the above-described systems. The implantable device 1458, upon detection of a neurological event may alert a remote monitoring location via local remote box 1452 (as described in U.S. Pat. No. 5,752,976), telephone 1454 and phone lines 1456 or the patient's care provider via an RF link 1432 to a pager-sized remote monitor 1460 placed in other locations in the house or carried (i.e., belt worn) by the care provider 1462. The remote caregiver monitor 1460 may include audible buzzes/tones/beeps, vocal, light and/or vibration to alert the caregiver 1462 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate.

Probabalistic Treatment Therapy

Suppose that a subject with seizures is being treated with an open loop control program. This subject may be simultaneously monitored using some means to log seizures. Example means include but are not limited to:

a. Quantifying the signal's seizure content using a method such as the algorithm in U.S. Pat. No. 5,995,868, without necessarily using the output to effect changes in real-time;

b. Logging time of seizure occurrences as well as brain state (e.g., awake); physical state (e.g., inactive); cognitive status (e.g., inattentive); metabolic status (e.g., blood glucose concentration); brain and body temperature; time from previous seizure(s); previous seizure(s)' intensity, severity and spread; and exposure to precipitants (e.g., light as measured using a light meter), without necessarily using the data to effect changes in real-time. Other markers of cerebral excitability such as GABA and glutamate concentrations and others listed in U.S. Pat. No. 6,934,580 may be included in the estimation of seizure probability; and/or c. an event button with clock and memory.

Let t=time elapsed since beginning of delivery of a particular therapy program. Let $\{t_i | i=1, 2, \ldots\}$ be a sequence of reference time points ("fiducial times"). Let $t_{REL} = t \pmod{\max\{t_i | t_i <= t\}}$. Here $t_{REL}$ corresponds to the time elapsed since the most recent fiducial time. Examples:

a. $t_i$=sequence of times corresponding to midnight on each day of monitoring. Then $t_{REL}$ is simply the time of day.
b. $t_i$=sequence of times corresponding to beginning of menses in a female subject. Then $t_{REL}$ is the time in the subject's menstrual cycle.
c. $t_i$=sequence of times corresponding to beginning of each administration of treatment or intervention. Then $t_{REL}$ is the time elapsed since the beginning of the last stimulation.
d. $t_i$=sequence of seizure start (or end) times. Then $t_{REL}$ is the time elapsed since the start (resp., end) of the last seizure.

At any point in time, the probability of a seizure occurring is given by P(t)=P(Sz occurring at time t). Knowing P(t) would be of value in treating epilepsy. The inventors have developed a framework that does not rely on conventional on-line, real-time seizure detection or prediction but utilizes available information (history) to issue warnings and/or deliver therapy based on this developed probability function (as opposed to specific, binary, event detections). This probability function and related decisions of whether or not to issue a warning or deliver therapy can incorporate useful dependency of factors such as type of present activity and its inherent risk of injury, social embarrassment, and importance to preserve cognitive functions.

For any relative time, $\tau$ in Range$\{t_{REL}\}$, given a reasonable length of monitoring, T, of the subject utilizing the current control program, one may compute and use the empirical probability of a seizure occurring at any point in time for this subject as:

$$p_E(\tau;T) = (\text{\# of seizures with } t_{REL}=\tau)/(\text{\# of times } t_{REL}=\tau).$$

This "empirical probability density of seizures relative to time with respect to a fiducial sequence" is an approximation of the unknown probability of interest, namely, P(Sz occurring at time $t_{REL}=\tau$).

This empirical probability function can be used to compare one therapy control program against another (or against the untreated subject) in order to determine which is more effective and enables adjustment of therapy to improve efficacy.

ILLUSTRATIVE EXAMPLES

Figure 7:
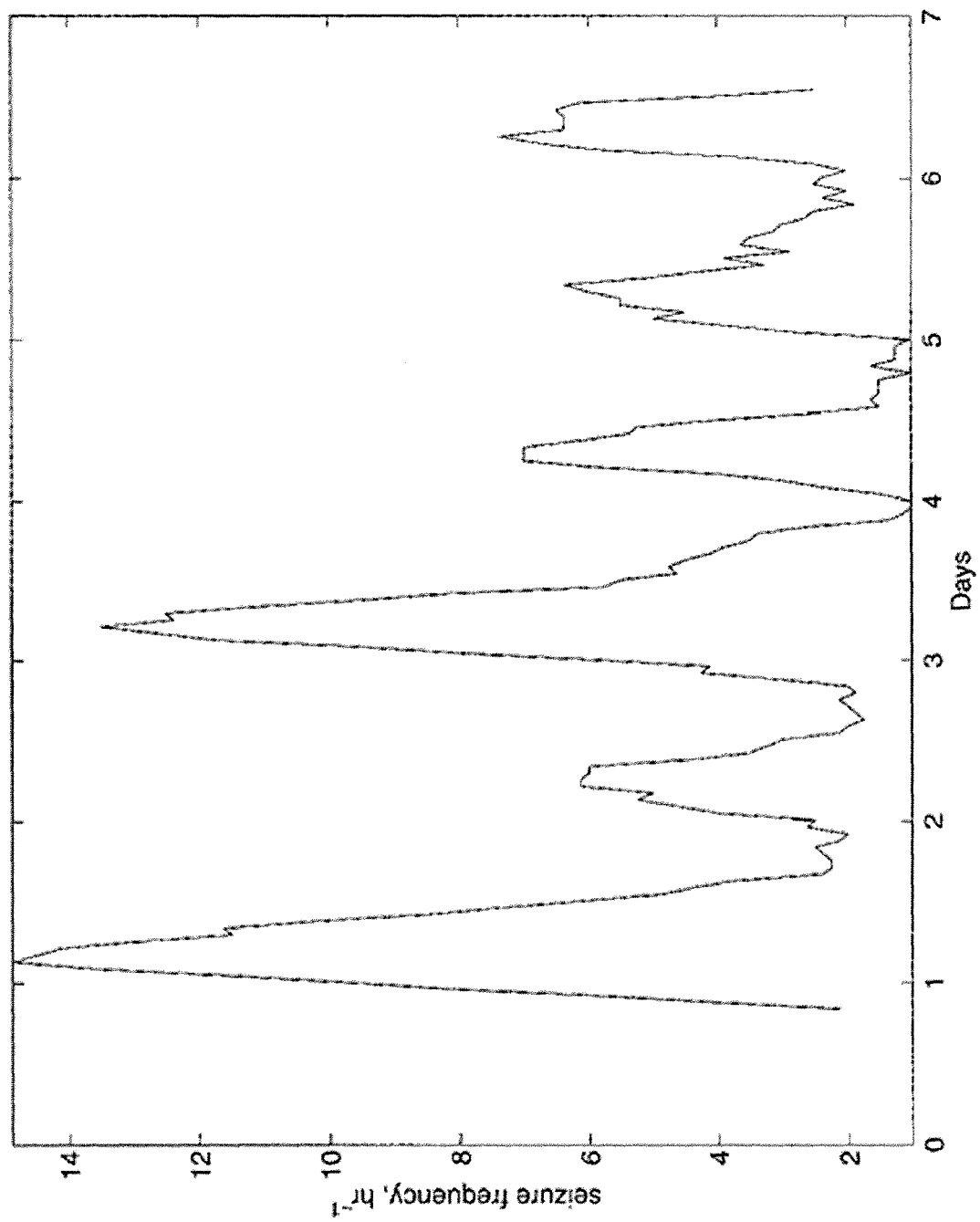
FIG. 7 is a chart of seizure frequency as a function of time of day in some subjects.

As depicted in FIG. 7, the probability of seizure occurrence is known to change as a function of time of day (from Osorio I, Frei M G, Manly B F J, Sunderam S, Bhavaraju N C, and Wilkinson S B. J Clin Neurophysiol. 2001 November; 18(6): 533-44). Moreover, it is known that some patients are much more likely to have seizures while they are asleep ("nocturnal epilepsy"). By examining seizure frequency of occurrence as a function of time of day, one can determine the effect of circadian variations on seizures for a particular subject and use this information to better control their seizures as illustrated in the following example.

Example 1

Figure 8:
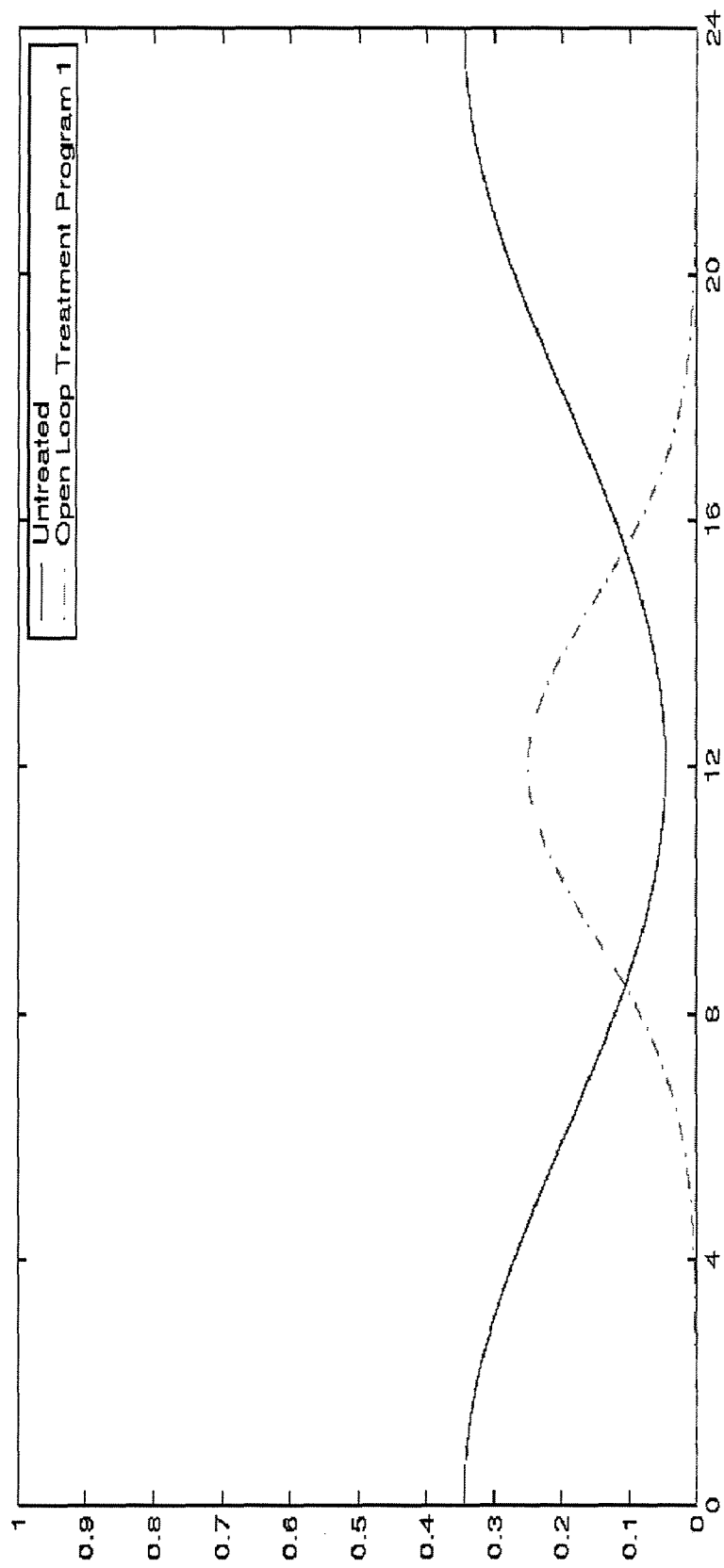
FIG. 8 is a chart of simulated probability of seizure as a function of time of day, for a supposed patient.

Suppose a subject with primarily nocturnal seizures is monitored continuously for one month (or some period of time that yields a representative or useful sample) with no therapy enabled, and then for a second month (or other period), while being treated with an open loop control program that consists of 5 mA of stimulation at 100 Hz for 1 minute every 10 minutes (i.e., on 1 minute, off 9 minutes). Using time-of-day in generating $t_{REL}$ (as in above example), the graphs in FIG. 8 illustrate $p_E(\tau)$ for months 1 (solid) and 2 (dash-dot), respectively. In this example, it is apparent that the therapy program had a seizure-reduction effect during the night, but may have increased seizure frequency during the day. Given this information, the user (subject or caretaker) may improve the overall efficacy of therapy by developing a new control program that is obtained by combining the approaches to produce a second control program that is equal to the previous one (on 1 minute, off 9 minutes) during the night, but is off completely between 8:30 and 15:30. Under the assumption that the effect of therapy is relatively instantaneous and lacking significant temporal carry-over effect, this revised control can be expected to result in improved therapy for the subject. While one skilled in the art will appreciate that the aforementioned assumptions need not be valid, the information obtained from the method allows the user to quantify the linearity of the response and the size and duration of the carry-over effect and to suitably modify the control program.

Figure 9:
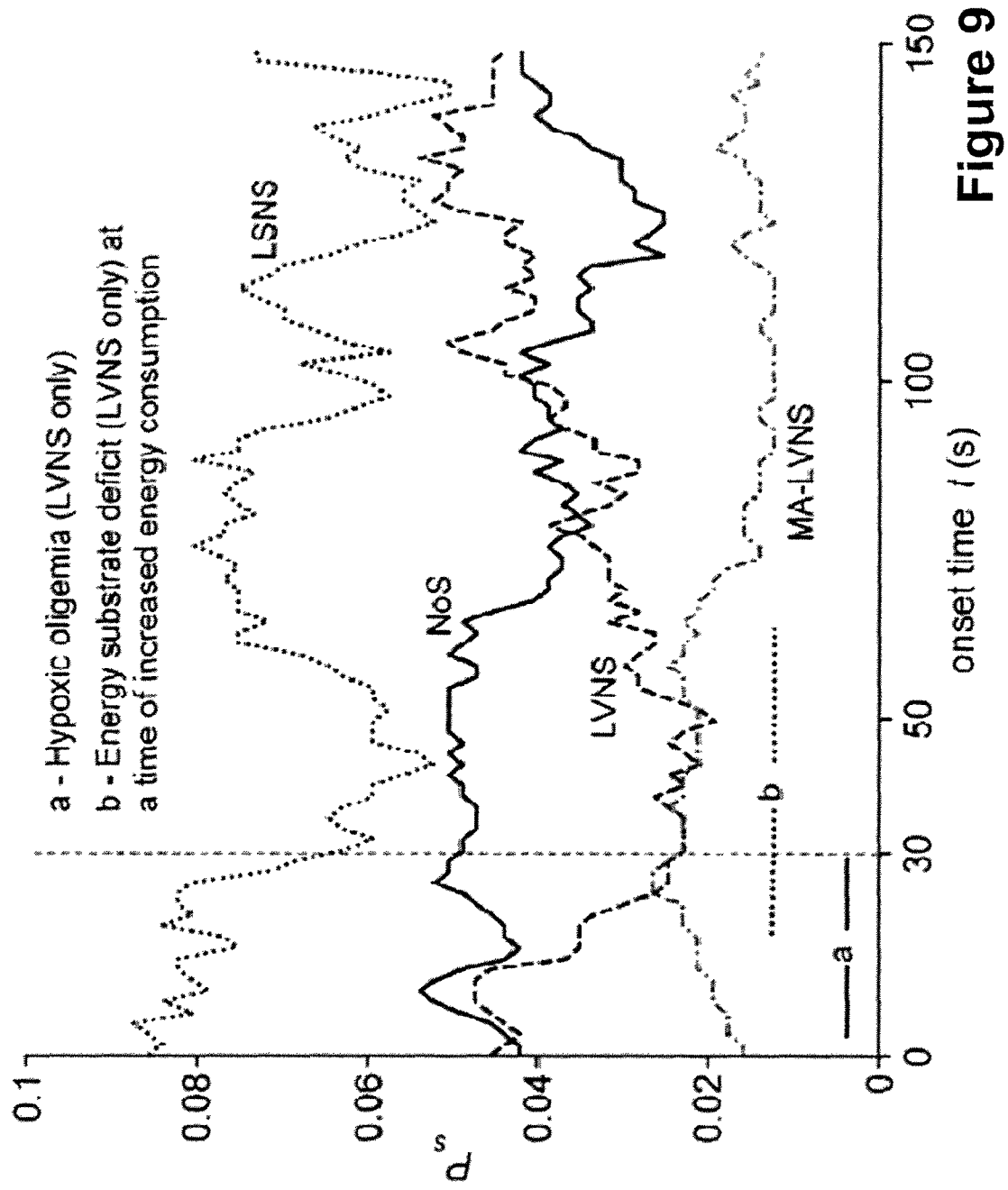
FIG. 9 is a chart of probability of seizures as a function of time during a stimulation cycle in some subjects.

FIG. 9 depicts observed changes in seizure duration and intensity as a function of time from onset of stimulation (from S. Sunderam et al., Brain Research 918 (2001) 60-66). In another embodiment, the times of stimulation are used as fiducial times to examine the effect on seizure longevity and optimize the stimulation parameters. Seizure probability and severity may also be estimated as a function of time of delivery of therapy (such as electrical stimulation) and may depend upon other relevant parameters such as intensity, duration, frequency, stimulation polarity, etc.

Example 2

Figure 10:
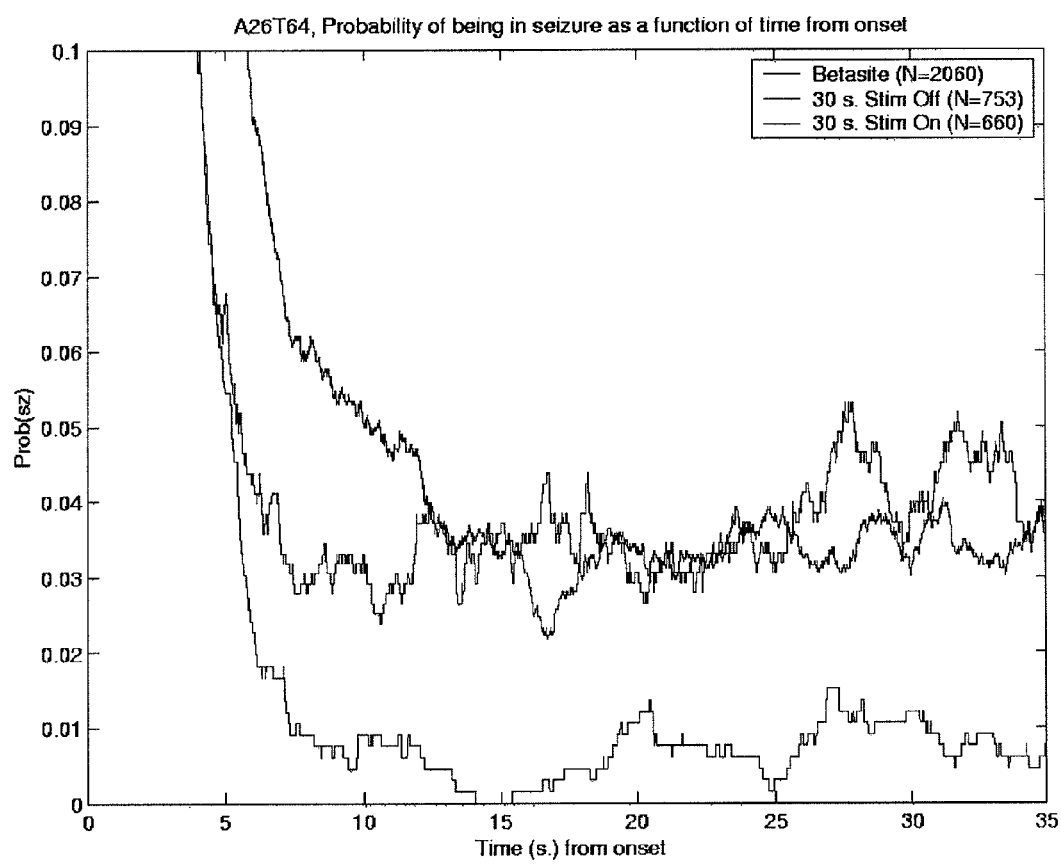
FIG. 10 is a chart of probability of seizures as a function of time from onset of stimulation in some subjects.
Figure 11:
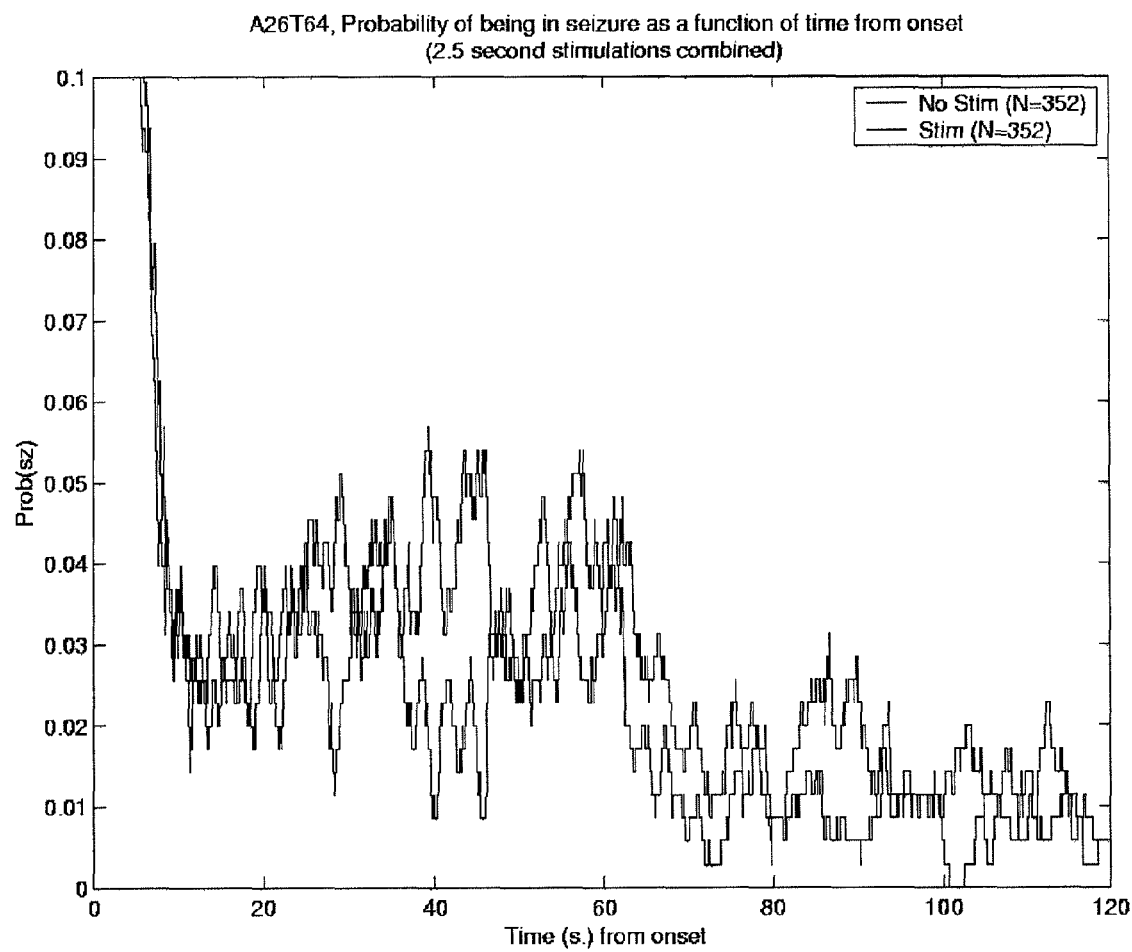
FIG. 11 is a chart of probability of seizures as a function of time from beginning of seizure in some subjects.

Consider a subject that is being treated with a closed-loop stimulation program. For example, after a period of no therapy, the treatment program provides for 2.5 s of continuous stimulation to the anterior thalamic nucleus, triggered by every other seizure detection (generated by an automated seizure detection algorithm). The subject continues to have seizures, so the stimulation duration is increased to 30 s of continuous stimulation, administered to the same brain location, again triggered by every other seizure detection. After a period of time, the monitoring data is collected and analyzed as described above with the fiducial times equal to the starting time of each stimulation. The corresponding probabilities of seizure survival, relative to elapsed time from start of stimulation, are shown in FIGS. 10 and 11. In this manner, the system enables the user to determine the duration of stimulation that has optimal effect in terms of seizure reduction (approximately 15 s), beyond which efficacy is not improved further.

FIG. 10, depicts a subject where every other seizure is treated by 2.5 s stimulation beginning at seizure onset. The curves show probability of being in seizure as a function of time from beginning of seizure. The upper curve indicates probability for stimulated seizures, and the lower curve represents those seizures that were not stimulated. No significant difference is evident.

In FIG. 11, depicts a subject where every other seizure is treated by 30 s stimulation beginning at seizure onset. The curves show probability of being in seizure as a function of time from beginning of seizure. The lowest curve indicates probability for stimulated seizures, the middle curve indicates probability for those seizures that were not stimulated, and the highest curve indicates the baseline probability from pre-treatment phase recordings.

Example 3

A subject that is being treated with an open-loop therapy may be equipped with a device for intensive continuous monitoring of biological signals (such as EEG or EKG), which will detect and quantify features of these signals (e.g., epileptiform brain activity or heart rate changes) associated with seizures for a period of time (e.g., 48 hr). The monitored activity will be analyzed with respect to some fiducial time sequence (e.g., times of onset of stimulation delivery, times of changing of stimulation intensity, time of day, etc.) and the empirical probability density of seizures relative to time with respect to the fiducial sequence is generated.

Figure 12:
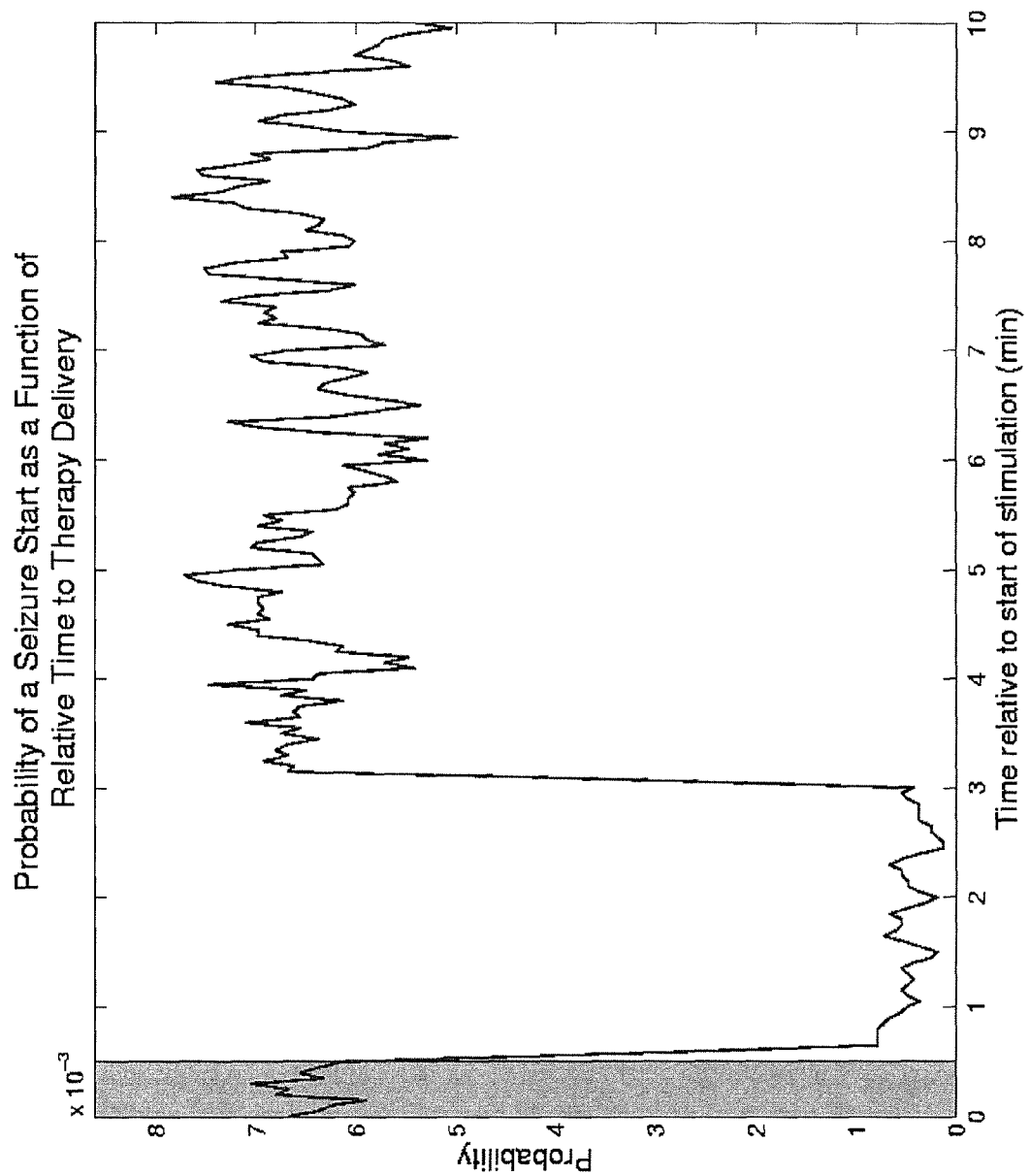
FIG. 12 is a chart of probability of seizures as a function of time relative to therapy delivery in some subjects.

FIG. 12 provides an illustration of such information, in which the fiducial times are the times of onset of trains of electrical stimulation delivered for 30 s every 10 minutes. From this analysis it becomes apparent that the open-loop stimulation program provides very little immediate effect, but has a carry-over, protective effect against seizures that lasts for 2.5 minutes beyond the end of stimulation. This implies that the open-loop stimulation program should be altered to provide 30 s of stimulation every 3 minutes. Similar subsequent analysis can be used to determine the potential benefit of additional fine-tuning of the therapy program.

The approach illustrated in the above example can be indirectly tested in future open-loop trials, by measuring changes in seizure frequency over pre-specified time periods as a function of stimulation cycle length (e.g., 1 min ON-5 min OFF vs. 1 min ON-2.5 min OFF); greater reductions in seizure frequency with shorter off cycles than with longer off cycles would demonstrate the direction and benefit of utilizing "carry-over" effect information in seizure prophylaxis or abatement.

The intervention delivered by the probabilistic closed-loop methods disclosed herein may be tailored for individual or subject-specific warning and/or treatment based on the frequency and/or severity of seizures, circadian patterns, occupational hazards, social factors, employment demands, etc.

The probabilistic closed-loop approach, which encompasses the concept of "intelligent open-loop," may be used to issue "graded" or incremental warnings and/or therapy. For example, the seizure probability in a given patient is estimated to be 40% at a given time. This probability estimate may trigger a warning (vibration or sound) that is half as intense as one associated with a probability twice as high (i.e., 80%). The intensity or type of warning in this embodiment changes as a function of changes in probability, either decreasing or increasing as a function of its value. Further, a warning associated with a certain probability estimate may change as a function of risk of injury or of social embarrassment should a seizure occur; a 40% seizure probability in a patient sitting in a chair at home would be much less intense than if the subject was operating a vehicle. Temperature sensors, accelerometers and/or EKG among other means, may be used to determine the level of activity (sedentary vs. in motion) and its relative duration to automatically adjust the level or type of warning. Operation of power equipment or of vehicles may be factored into the warning scale by the patient simply pressing a button prior to initiating these activities. Cars or power equipment may be also equipped with devices that upgrade the warning level as they are turned ON and a disabling device that communicates with the patient's device may be activated should the seizure probability be at an unsafe level. An identical approach may be taken for therapy: The type of therapy and parameters/dose used when the seizure probability is 40% may be different that when it is 80% or when the subject changes activity from a low to a high risk for injury.

In other embodiments, other thalamic stimulation targets may be applied for treatment of the neurological disorder, including particularly mesial temporal and mesial frontal intractable epilepsies. These targets include N. Reticulatus polaris and N. Lateropolaris.

In still other embodiments, evoked responses may be used to assess the precision of lead placement intra- and inter-individually. This complements MRI or other imaging based techniques and is particularly useful for targets that as the ATN, than unlike the STN (for treatment of movement disorders) appear to lack easily identifiable electrophysiological markers. Accurate in-vivo localization of electrodes/contacts and identification of functional or electrographic target markers loom as challenges that must be successfully addressed to identify, with reproducible accuracy in humans, structures with seizure gating capabilities and properly assess the therapeutic value/ratio of open- or closed-loop electrical stimulation. Although evoked responses techniques as used in a recent investigation, do not provide direct information about lead localization, they may be used (a) to indirectly determine if the Epileptogenic Zone(s) and the leads' targets share anatomical connections; and (b) as tools to assess intra- as well as inter-individual uniformity/precision of lead placement. The intra- and inter-individual differences in evoked responses in these subjects, accurately predicted the probable differences in lead location. The basis for this claim is that the potential or waveform (defined by polarity, morphology and amplitude) at any location in the brain may depend on: (1) the nature, location and orientation of the current sources; and (2) volume conduction characteristics which are determined by the electrical and geometric properties of the tissue. That is, potentials or waveforms of different amplitude, morphology and polarity, recorded from the same site, are not generated by the same current source or structure. Indirect or direct electrical stimulation of brain structures generates reproducible waves or oscillations (i.e., evoked responses), that may be recorded from the scalp (or intra-cerebrally) and have shapes and latencies that are unique for each structure. For example, the responses generated by stimulation of structures involved in the processing of sensory signals, have characteristic shapes and latencies that are highly similar among different subjects and are easily distinguishable, from those generated by structures involved in processing acoustic stimuli which are also highly similar inter-individually. It follows, that direct or indirect stimulation of the same structure in each cerebral hemisphere, elicits identical if not highly similar reproducible responses that may be recorded from the scalp, using electrodes placed according to the 10-20 system, or, any other standardized system of electrode placement. These responses may be also reliably and reproducibly recorded intra-cerebrally, from structures connected to those being stimulated. Differences in evoked responses elicited from relatively selective unilateral electrical or chemical stimulation of a given cerebral structure, compared to a) responses elicited by stimulation of the homologous contra-lateral structure or b) responses elicited in other individuals, suggest the structures being stimulated are different. Thus, the leads through the currents are being passed, and are not in homologous structures or regions. This allows safe, repetitive and accurate assessment of precision of placement without the need to resort to magnetic resonance or computerized tomography, also reducing the subjectivity inherent to visual localization of leads since evoked responses are quantitative.

The usefulness of the invention should be apparent to one skilled in the art. The use of any and all examples or exemplary language herein (e.g., "such as") is intended merely to better illuminate the invention and does not pose a limitation on the scope of the invention unless otherwise claimed. No language in the specification should be construed as indicating any non-claimed element as essential to the practice of the invention.

The present invention has sometimes been described in terms of preferred and illustrative embodiments thereof. Numerous other embodiments, modifications and variations within the scope and spirit of the appended claims will occur to persons of ordinary skill in the art from a review of this disclosure.

What is claimed is:

1. A method for treating a patient with a neurological disorder, comprising:
   using one or more processors to determine a probability of a seizure occurring in the patient at a selected time point as a function of historical data comprising
      a set of reference time points,
      a relative time elapsed from one of the reference time points to the selected time point, and
      seizure activity observed at one or more moments when the relative time had elapsed from one or more of the reference time points, and
   treating the patient based on the determined probability, wherein treating the patient comprises at least one of evaluating the patient, diagnosing the neurological disorder of the patient, comparing therapies for the patient, alerting the patient, alerting a caregiver, dosing the patient with an implantable medical device, and stimulating the patient with the implantable medical device.

2. The method of claim 1, wherein the probability of a seizure occurring in the patient is determined according to a probability function $P_E$ as follows:

$$P_E(\tau; T) = \frac{\text{Seizures}(t_{REL} = \tau)}{\text{Observations}(t_{REL} = \tau)}$$

wherein
   $\tau$ is the relative time elapsed from the one reference time point to the selected time point,
   T is a monitoring period during which the set of reference time points were recorded,
   Seizures($t_{REL}=\tau$) is a number of seizures observed at the one or more moments when the relative time $\tau$ elapsed from one or more of the reference time points, and
   Observations($t_{REL}=\tau$) is the number of recorded observations at the one or more moments when the relative time $\tau$ elapsed from one or more of the reference time points.

3. The method of claim 1, wherein the reference time points each correspond to a respective therapy delivery.

4. The method of claim 1, wherein the reference time points each correspond to a time of a respective day.

5. The method of claim 1, wherein the reference time points each correspond to a respective seizure.

6. The method of claim 1, wherein the set of reference time points is generated from two or more temporally discontinuous recording time periods.

7. The method of claim 1, further comprising determining, based on the determined probability, a therapeutic carry-over effect persisting beyond cessation of a past delivered therapy and delivering a subsequent therapy based on the determined therapeutic carry-over effect.

8. The method of claim 7, further comprising providing event detection-contingent therapy in response to detecting at least one of a pre-seizure state and a seizure state.

9. The method of claim 1, further comprising determining, based on the determined probability, a therapeutic carry-over effect persisting beyond cessation of a past delivered therapy and delivering a subsequent series of therapies based on the determined therapeutic carry-over effect.

10. A method for treating a patient with a neurological disorder, comprising:
    using one or more processors to determine a probability of a seizure occurring in the patient after a delivered therapy, the determined probability being a function of historical data comprising
       a set of reference time points correlated to respective past delivered therapies,
       a relative time elapsed from one of the reference time points, and
       a number of seizures occurring at one or more moments when the relative time had elapsed from one or more of the reference time points;
    determining a therapeutic carry-over effect based on the determined probability, the therapeutic carry-over effect persisting beyond cessation of the delivered therapy; and
    treating the patient based on the determined probability, comprising delivering a subsequent therapy based on the determined therapeutic carry-over effect.

11. An apparatus for treating a patient with a neurological disorder, comprising:
    a signal monitoring element for sensing patient activity and outputting a corresponding signal;
    a treatment delivery element for delivering treatment to the patient; and
    one or more processors configured to
    determine a probability of a seizure occurring in the patient at a selected time point as a function of historical data comprising
       a set of reference time points,
       a relative time elapsed from one of the reference time points to the selected time point, and
       seizure activity observed at one or more moments when the relative time had elapsed from one or more of the reference time points, and
    control treating the patient based on the determined probability, wherein treating the patient comprises at least one of evaluating the patient, diagnosing the neurological disorder of the patient, comparing therapies for the patient, alerting the patient, alerting a caregiver, dosing the patient, and stimulating the patient.

12. The apparatus of claim 11, wherein the probability of a seizure occurring in the patient is determined according to a probability function $P_E$ as follows:

$$P_E(\tau; T) = \frac{\text{Seizures}(t_{REL} = \tau)}{\text{Observations}(t_{REL} = \tau)}$$

wherein

τ is the relative time elapsed from the one reference time point to the selected time point, T is a monitoring period during which the set of reference time points were recorded, Seizures($t_{REL}$=τ) is a number of seizures observed at the one or more moments when the relative time τ elapsed from one or more of the reference time points, and Observations($t_{REL}$=τ) is the number of recorded observations at the one or more moments when the relative time τ elapsed from one or more of the reference time points.

13. The apparatus of claim 11, wherein the reference time points each correspond to a respective therapy delivery.

14. The apparatus of claim 11, wherein the reference time points each correspond to a time of a respective day.

15. The apparatus of claim 11, wherein the reference time points each correspond to a respective seizure.

16. The apparatus of claim 11, wherein the set of reference time points is generated from two or more temporally discontinuous recording time periods.

17. The apparatus of claim 11, wherein the one or more processors are further configured to determine, based on the determined probability, a therapeutic carry-over effect persisting beyond cessation of a past delivered therapy and control delivering a subsequent therapy based on the determined therapeutic carry-over effect.

18. The apparatus of claim 17, wherein the one or more processors are further configured to control event detection-contingent therapy in response to detecting at least one of a pre-seizure state and a seizure state.

19. The apparatus of claim 11, wherein the one or more processors are further configured to determine, based on the determined probability, a therapeutic carry-over effect persisting beyond cessation of a past delivered therapy and control delivering a subsequent series of therapies based on the determined therapeutic carry-over effect.

20. An apparatus for treating a patient with a neurological disorder, comprising:

a signal monitoring element for sensing patient activity and outputting a corresponding signal;

a treatment delivery element for delivering treatment to the patient; and one or more processors configured to determine a probability of a seizure occurring in the patient after a delivered therapy, the determined probability being a function of historical data comprising a set of reference time points, a relative time elapsed from one of the reference time points to the selected time point, and seizure activity observed at one or more moments when the relative time had elapsed from one or more of the reference time points, determine a therapeutic carry-over effect based on the determined probability, the therapeutic carry-over effect persisting beyond cessation of the delivered therapy, and control treating the patient based on the determined probability, the treating the patient comprising delivering a subsequent therapy based on the determined therapeutic carry-over effect.

* * * * *